July 17, 1923. Re. 15,657
G. A. McMILLEN
HERNIAL TRUSS
Original Filed Feb. 19, 1917
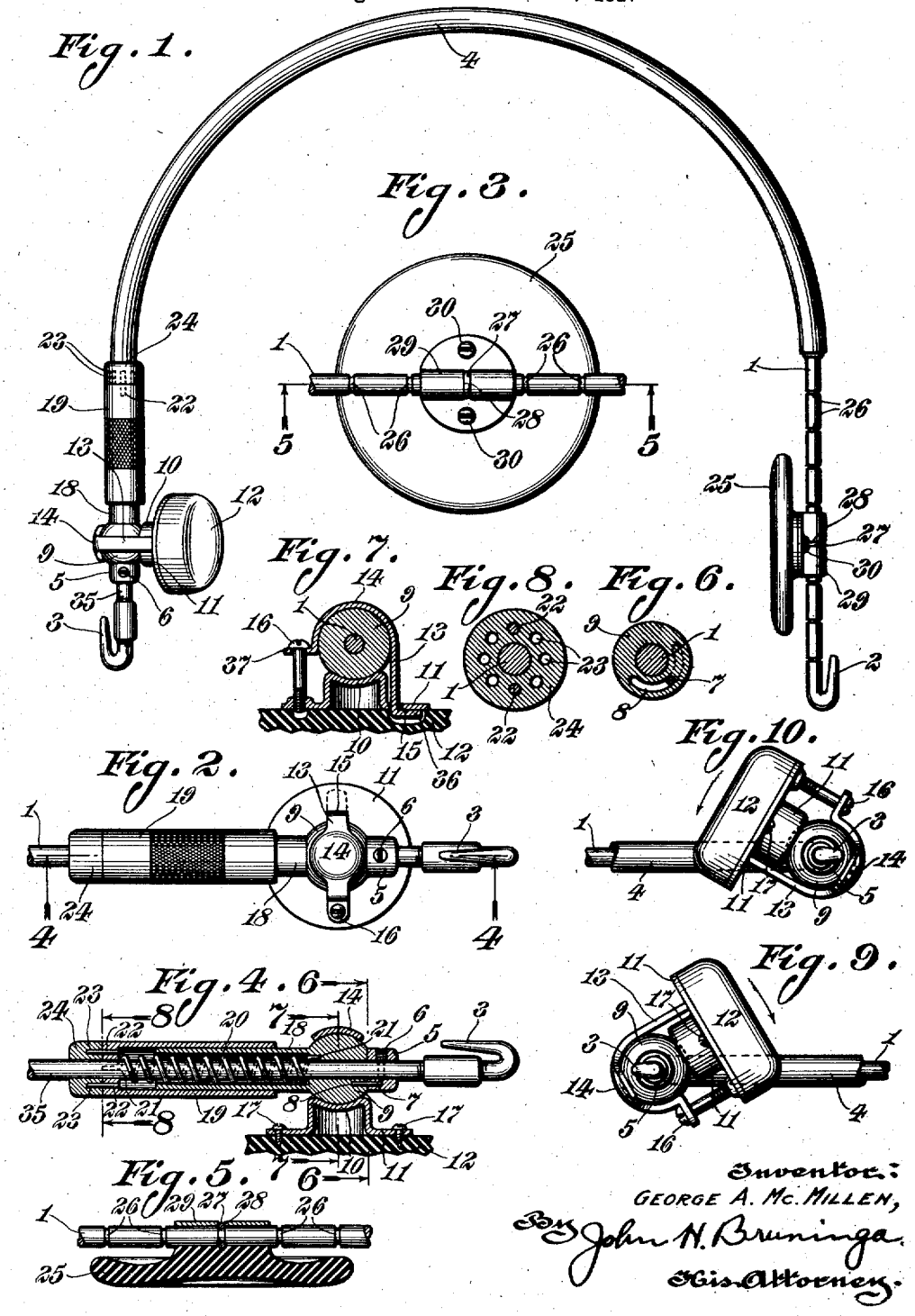
Inventor:
GEORGE A. McMILLEN,
By John N. Bruninga,
His Attorney.

Reissued July 17, 1923. Re. 15,657

UNITED STATES PATENT OFFICE.

GEORGE A. McMILLEN, OF ALTON, ILLINOIS.

HERNIAL TRUSS.

Original No. 1,237,667, dated August 21, 1917, Serial No. 149,612, filed February 19, 1917. Application for reissue filed March 13, 1919. Serial No. 282,513.

*To all whom it may concern:*

Be it known that I, GEORGE A. McMILLEN, a citizen of the United States, and a resident of Alton, in the county of St. Clair, State of Illinois, have invented new and useful Improvements in Hernial Trusses, of which the following is a specification.

This invention relates to hernial trusses adapted for the treatment and relief of ruptures. Ruptures occur in various positions in the abdominal walls, and accordingly, the required truss must not only fit the body of the patient, but the pad must be adjusted to correspond to the position of the rupture. In any adjusted position, the pad must apply a yielding upward pressure on the rupture in order to properly perform its supporting function and this action must be obtained whether the rupture is a right or a left one.

One of the objects of this invention, therefore, is to provide a truss which is of universal application and which can be not only adjusted for right and left ruptures, but also in accordance with the size of the patient and the position of the rupture.

A further object of this invention is to provide improved means for attaching the pad as well as the back disk to the bowed truss-wire or spring, in such a manner that the said pad will more perfectly fit the rupture and support the same automatically during the various movements of the body, whereby the truss will be more comfortable and efficient during use.

A further object of this invention is to provide a surgical truss in which novel means for supporting and adjusting the pad are made use of, together with a novel arrangement of a torsional retaining-spring adapted to be tensioned as delicately as desired, and which is designed to act upon the pad-support, after the latter has been adjusted, to automatically maintain the pad yieldingly yet comfortably in contact with the rupture.

A further object of this invention is to provide an improved and automatically adjustable back-disk which is connected with the supporting wire or spring by novel and efficient means which will allow of its adjustment to fit lean and stout persons with the same supporting wire, and to automatically maintain its pivotal connection with said wire during all the various movements of the body of the wearer.

Further objects will appear from the detail description taken in connection with the accompanying drawing, in which:

Figure 1 is a plan of a truss embodying this invention;

Figure 2 is an enlarged detail side elevation of the pad and its connections;

Figure 3 is an enlarged detail side elevation of the back disk embodying this invention;

Figure 4 is a section on the line 4—4, Figure 2;

Figure 5 is a section on the line 5—5, Figure 3;

Figure 6 is an enlarged section on the line 6—6, Figure 4;

Figure 7 is a section on the line 7—7, Figure 4;

Figure 8 is an enlarged section on the line 8—8, Figure 4;

Figure 9 is a detail front elevation of Figure 1, showing the pad in position to treat right ruptures; and Figure 10 is a view similar to Figure 9, but showing the pad in position to treat left ruptures.

Referring to the accompanying drawing, and more particularly to Figures 1, 2, 4 and 6 to 9 inclusive, 1 designates a supporting band which is, in this case, in the form of a bowed wire or spring, provided with a hook 2 at one of its ends and with a hook 3 at its opposite end detachably secured in place by having its internally threaded body engaging the threaded end of shank 35 of the supporting band. The usual sheath 4 of rubber or other suitable material is provided for said supporting band for an obvious purpose.

A collar 5 is fixed upon the shank 35 by means of a set screw 6 at a point adjacent the hook 3, and this collar carries a stop pin 7 which projects from the inner face of the collar in a direction parallel with the shank 35 and engages a slot or recess 8 in a carrier, which is rotatively mounted on the shank and has its end formed to provide a ball 9. The pin and slot therefore permit limited rotative movement of the carrier on the shank.

The outer surface of the ball 9 is spherical in form and is engaged by a socket 10 formed in a base plate 11 secured to a pad 12, which pad may be of the usual form and faced with leather. Cooperating with the socket 10 is a U-shaped loop 13 having a socket 14 of spherical form located diametrically opposite the socket 10. One end of the loop or stirrup is flexibly connected to the base plate and is readily detachable therefrom by having a bent portion 36 loosely engaging in a slot 15 formed in a base plate; the other end of the loop is flexibly connected to the base plate by means of an adjusting and clamping screw 16 passing loosely through a perforation formed in an ear 37 on the loop and having a threaded connection with the base plate. With this construction, the screw 16 is adapted to draw the loop against the base plate so as to firmly clamp the ball in the sockets formed by the base plate and loop. With this construction, therefore, the pad can be adjusted on the carrier transversely and along the axis of the band and shank, and can be clamped and firmly secured in any desired adjusted position. The base plate is secured to the pad by means of screws 17.

The carrier is provided with a tubular shank 18 which extends inwardly along the shank. A shifting element 19, in the form of a sleeve closed at one end, is mounted to slide and rotate relative to the carrier on the shank. A coiled spring 20 encircles the shank 35 and is housed within the tubular shank 18 and the sleeve 19 and bears at one end against the carrier and at its other end against the shifting element. The ends of this spring are bent axially as shown at 21 and are fixed within holes or recesses in the ends of the carrier and the shifting element. The spring, is, therefore, connected at one end to the carrier and at its other end to the shifting element forming an abutment for the spring.

The shifting element is provided with one or more axially projecting pins 22 adapted to engage with a series of axial recesses 23 arranged circumferentially of a collar 24 fixed to the shank 35 and forming a stop for the shifting element.

Assuming that the spring is under tension, this spring will act on the carrier to rotate it until one end of the slot 8 therein engages with the pin 7 on the collar 5 fixed to the shank 35. This will place the pad in the position where it exerts an upward yielding pressure on the rupture, the pad being movable in the direction of the arrow against the yielding tension of the spring through limited distances determined by the length of the slot 8, but its movement in either direction and especially in the upward direction, being limited by the engagement of the end of the slot with the pin 7 as shown in Figure 6. The result is, therefore, that the pad will always exert a yielding upward pressure on the rupture as is desirable and necessary. It will, of course, be understood that the supporting band is retained in position on the body of the patient and that the other end of the band has a back disk 25 attached thereto in a manner hereinafter to be described.

In order to vary the tension of the spring so as to adjust the pressure of the pad on the rupture in accordance with conditions, the shifting element 19 is adjusted relatively to the carrier on the shank to increase or decrease the spring tension as desired. In order to permit such adjustment, the shifting element which is knurled, as shown in Figures 1 and 2, is moved to the right Figures 2 and 4, until the pins 22 are free of the recesses 23; the shifting element is then rotated in the desired direction until the proper adjustment is obtained and the pins are then allowed to snap into the nearest set of recesses 23. The adjustment being completed, the parts are firmly retained in adjusted positions.

In order to adapt the truss for either right or left ruptures, the inclination of the pad must be reversible so as to always exert a yielding upward pressure. Thus, it will be seen that where as in Figures 1 and 9, the truss is adapted for a right rupture, if the pad is placed on the left side by turning the truss over, the inclination of the pad must be reversed as shown in Figure 10. This can be accomplished by the construction embodying this invention. It will be noted that the ends 21 of the spring are fixed respectively in the carrier and shifting element and that the spring is adapted to apply a yielding tension whether coiled or uncoiled. Accordingly, to adjust the device to a left rupture, the shifting element is moved to the right, Figure 2, until the pins 22 are free of the recesses 23, and the element is then rotated on its supporting shank until the tension of the spring is entirely relieved; the rotation of the shifting element is then continued through a suitable angle so as to apply a yielding tension to the spring in the opposite direction, thereby causing the carrier to shift rotatively until the other end of the slot 8 engages the pin 7 as shown in dotted lines 6, thereby shifting the pad to the position shown in Figure 10. In this shifted position of the pad, a yielding upward pressure will be applied to a left rupture.

It will, therefore, be seen that in accordance with this invention, the pad is positioned on the supporting band so as to adapt it for right and left ruptures, and means are provided for selectively positioning the pad for such right and left ruptures and to apply a yielding upward pressure to the rupture in either of these positions. This can be accomplished without disassembling the truss and without disturbing any of the permanent connections; accordingly, the adjustments can be made by an ordinary druggist and without any tools. Moreover, the mounting of the pad on the carrier permits universal adjustment of the pad so as to adapt the truss to the various conditions encountered in the particular case under consideration. In any position of adjustment, the pad will be yieldingly retained so as to yield in accordance with the movements of the body.

A back disk 25 made of hard rubber or the like is mounted for movement axially and rotatively on the shank terminating in the hook 2. This hook is provided with a series of annular grooves 26 adapted to be engaged by a split ring 27 of spring metal. Encircling the shank and attached to the back disk by means of screws 30 is a clip 29 adapted to form a bearing for mounting the back disk for axial and rotative movement on the shank. This clip is provided intermediate its ends in the bearing portion with a recess 28 adapted to receive the resilient split ring 27, which ring is also located in a groove in the bearing portion of the back disk so that this spring is permitted to expand and contract in its mounting in the back disk and the clip.

In any position of adjustment with the split ring engaging one of the grooves, the back disk is held against axial movement but is permitted rotative movement on the shank although retained by a light frictional action of the split ring and the bearing. In order to shift the back disk to any other adjusted position, the back disk is forcibly grasped and moved axially. This causes the rounded inner edges of the split ring by engagement with the edges of the groove 26 to cause the ring to expand and mount the body of the ring until the next groove is engaged, when the ring will snap into this groove and hold the parts in adjusted position. The back disk can, therefore, be adjusted to the body of the patient in a simple and effective manner.

It is obvious that various changes may be made in the details of construction without departing from the spirit of this invention; it is, therefore, to be understood that this invention is not to be limited to the specific construction shown and described.

Having thus described the invention, what is claimed is:

1. An improved truss, comprising the usual supporting wire or bowed spring; a ball mounted loosely on said wire, to slide and rotate; a fixed part on said wire adjacent said ball; a connection between said ball and said fixed part, for limiting the rocking movement of said ball; another fixed part on said wire on the opposite side of said ball, and separated a distance from said ball; a spiral spring mounted between said ball and the last-mentioned fixed part; and means for attaching one end of said spring to said ball and its opposite end in revoluble adjustment with relation to said last-mentioned fixed part, to vary the torsional power exerted by said spring upon said ball; in combination with a U-shaped loop having a ball socket in engagement with the said ball; a base-plate having a ball-socket in engagement with said ball, and clamped into contact with said ball by said loop, but adjustable on the ball to any angle desired; a hernial pad attached to said base-plate; and a back disk adjustably connected to said wire by means which permit said disk to rotate on said wire and be adjusted axially to fit a lean or stouter patient.

2. An improved truss, comprising the bowed supporting wire; two collars fixed on said wire at a distance from each other, the collar nearest the end of said wire having a stop-pin fixed in it and projecting therefrom in a direction toward the other fixed collar; a ball mounted on said wire to rock and slide adjacent said fixed collar which carries said stop-pin, said ball having formed in it a curved recess the opposite walls of which are engaged by said pin to limit the rocking movement of said ball; a tubular shank on said ball; a sleeve mounted on said tubular shank, to slide and to rock thereon; means for closing one end of said sleeve; a spiral spring having its ends fixed the one to said ball and the other to the means which closes the end of said sleeve, and said spring mounted on the said wire within said tubular shank and said sleeve; a pin fixed in the means which closes the end of said sleeve and projecting into one of a series of recesses formed in the adjacent fixed collar, whereby the torsional strain of said spring may be adjusted; a hernial pad adjustably connected to the said ball; and a back disk suitably connected to said wire.

3. A hernial truss, comprising, a supporting band, a pad mounted for movement thereon, means for selectively shifting said pad on said band to position and adapt it for right and left ruptures while the mounting of said pad on said band is maintained, and means adapted upon such shifting for yieldingly retaining said pad in either of said positions.

4. A hernial truss, comprising, a supporting band, a pad mounted for movement thereon, means for selectively shifting said pad on said band to position and adapt it for right and left ruptures while the mounting of said pad on said band is maintained, and means adapted upon such shifting for yieldingly retaining said pad, adapted to apply a yielding upward pressure on the rupture in either of said positions.

5. A hernial truss, comprising, a supporting band, a pad mounted for movement thereon, means for selectively shifting said pad on said band to position and adapt it for right and left ruptures while the mounting of said pad on said band is maintained, and means acting on said pad, adapted upon such shifting to apply a yielding upward pressure on the rupture in either of said positions.

6. A hernial truss, comprising, a supporting band, a pad mounted for movement about an axis along said band, and means for shifting said pad about said axis to position and adapt said pad to right and left ruptures, adapted upon such shifting to apply a yielding upward pressure on the rupture in either of said positions.

7. A hernial truss, comprising, a supporting band, a pad mounted for movement about an axis along said band, means for adjusting said pad in different shifted positions about said axis to position and adapt said pad to right and left ruptures, and means acting on said pad, adapted upon such shifting to apply a yielding upward pressure on the rupture in either of said positions.

8. A hernial truss, comprising, a supporting band, a pad mounted for movement about an axis along said band, a spring acting on said pad to apply a yielding pressure on the rupture, and means cooperating with said spring, constructed to shift said pad and adapt the same to right and left ruptures.

9. A hernial truss, comprising, a supporting band, a carrier mounted for movement thereon, a pad mounted on said carrier, means for shifting said carrier to adapt said pad to right and left ruptures, and means acting on said carrier, adapted upon such shifting to cause said pad to apply a yielding pressure on the rupture in either of said positions.

10. A hernial truss, comprising, a supporting band, a carrier mounted for movement thereon, a pad mounted on said carrier, a spring acting on said carrier, adapted to cause said pad to yieldingly engage said rupture, and means for shifting said carrier to adapt said pad to right and left ruptures, while the mounting of said pad on said band is maintained.

11. A hernial truss, comprising, a supporting band, a carrier mounted for movement thereon, a pad mounted for movement on said carrier, a spring acting on said carrier adapted to cause said pad to yieldingly engage the rupture, and means for shifting said spring while the mounting of said pad on said band is maintained, adapted to shift said carrier to adapt said pad to right and left ruptures.

12. A hernial truss, comprising, a supporting band, a carrier mounted for movement thereon, a pad adjustably mounted on said carrier, means for shifting said carrier to adapt said pad to right and left ruptures and means acting on said carrier, adapted upon such shifting to cause said pad to apply a yielding pressure on the rupture in either of said positions.

13. A hernial truss, comprising, a supporting band, a carrier mounted for movement about an axis along said band, a pad mounted on said carrier, means for shifting said carrier on said axis, and means adapted on such shifting for yieldingly retaining said carrier in any of said shifted positions.

14. A hernial truss, comprising, a supporting band, a carrier mounted for movement about an axis along said band, a pad adjustably mounted on said carrier, means for shifting said carrier on said axis, and means adapted on such shifting for yieldingly retaining said carrier in any of said shifted positions.

15. A hernial truss, comprising, a supporting band, a carrier mounted for movement about an axis along said band, a pad mounted on said carrier for adjustment about said axis, means for shifting said carrier on said axis, and means adapted on such shifting for yieldingly retaining said carrier in any of said shifted positions.

16. A hernial truss, comprising, a supporting band, a carrier mounted for movement about an axis along said band, a pad mounted on said carrier for adjustment transversely of said axis, means for shifting said carrier on said axis, and means adapted on such shifting for yieldingly retaining said carrier in any of said shifted positions.

17. A hernial truss, comprising, a supporting band, a carrier mounted for movement about an axis along said band, a pad mounted on said carrier for adjustment about and transversely of said axis, means for shifting said carrier on said axis, and means adapted on such shifting for yieldingly retaining said carrier in any of said shifted positions.

18. A hernial truss, comprising, a supporting band, a shank on said band, a carrier mounted for rotative movement on said shank, a pad on said carrier, and selectively acting means adapted to yieldingly retain said carrier selectively in either of two positions on said shank.

19. A hernial truss, comprising, a supporting band, a shank on said band, a carrier mounted for rotative movement on said shank, a pad on said carrier, a spring, and selectively acting means cooperating with said spring, adapted to yieldingly retain said carrier selectively in either of two positions on said shank.

20. A hernial truss, comprising, a supporting band, a shank on said band, a carrier mounted for rotative movement on said shank, a pad on said carrier, a spring connected with said carrier, and means for selectively tensioning said spring in either direction, adapted to yieldingly retain said carrier selectively in either of two positions on said shank.

21. A hernial truss, comprising, a supporting band, a shank on said band, a carrier mounted for rotative movement on said shank, a pad on said carrier, a spring, and selectively acting means for applying the tension of said spring to said carrier in either direction, adapted to yieldingly retain said carrier selectively in either of two positions on said shank.

22. A hernial truss, comprising, a supporting band, a shank on said band, a carrier mounted for rotative movement on said shank, a pad on said carrier, a spring connected with said carrier, an abutment for said spring, and selectively acting means for relatively shifting said abutment and said carrier, adapted to yieldingly retain said carrier selectively in either of two positions on said shank.

23. A hernial truss, comprising, a supporting band, a shank on said band, a carrier mounted for rotative movement on said shank, a pad on said carrier, a spring connected with said carrier, an abutment for said spring, and means for relatively shifting said abutment and said carrier axially on said shank, adapted to yieldingly retain said carrier selectively in either of two positions on said shank.

24. A hernial truss, comprising, a supporting band, a shank on said band, a carrier mounted for rotative movement on said shank, a pad mounted for universal adjustment on said carrier, a spring adapted to yieldingly retain said carrier on said shank, and means for controlling said spring while the mounting of said pad on said band is maintained.

25. A hernial truss, comprising, a supporting band, a shank on said band, a carrier mounted for rotative movement on said shank, a pad mounted for universal adjustment on said carrier, a spring acting on said carrier, and means for shifting said spring while the mounting of said pad on said band is maintained, adapted to yieldingly retain said carrier selectively in either of two positions on said shank.

26. A hernial truss, comprising, a supporting band, a shank on said band, a carrier mounted for rotative movement on said shank, a ball on said shank, a pad having a socket engaging said ball, and a spring adapted to yieldingly retain said carrier on said shank.

In testimony whereof I have hereunto set my signature.

GEORGE A. McMILLEN.